United States Patent [19]

Schwartz

[11] 4,270,540
[45] Jun. 2, 1981

[54] LAMINATED STRIP FOR SKIN THICKNESS CONTROL FOR USE WITH DERMATOME APPARATUS AND METHOD OF USING THE SAME

[76] Inventor: Boris Schwartz, 625 Lafayette Ave., Hawthorne, N.J. 07506

[21] Appl. No.: 140,827

[22] Filed: Apr. 16, 1980

[51] Int. Cl.³ .......................................... A61B 17/322
[52] U.S. Cl. ............................................... 128/305.5
[58] Field of Search ................... 128/305.5, 305, 304, 128/751, 757, 355; 30/280, 282

[56] References Cited

U.S. PATENT DOCUMENTS

| | | | |
|---|---|---|---|
| 1,594,613 | 8/1926 | Hagen | 128/305.5 |
| 2,288,709 | 7/1942 | Hood | 128/305.5 |
| 2,442,433 | 6/1948 | Reese | 128/305.5 |
| 4,098,278 | 7/1978 | Schwartz | 128/305.5 |

Primary Examiner—Kyle L. Howell
Assistant Examiner—Michael H. Thaler
Attorney, Agent, or Firm—Ralph R. Roberts

[57] ABSTRACT

This invention pertains to an improved dermatome hand held and operated apparatus in which an adhesive strip of material having a given width and length and of selected thickness is used with a razor blade type of cutter. The strip, as used with the dermatome apparatus, is much like that disclosed in applicant's U.S. Pat. No. 4,098,278 as issued July 4, 1978. The apparatus is like that shown in the referenced patent but includes a laminated portion that is selectively removed to provide a given thickness of strip and to thus provide a thickness of skin that is in an inverse ratio to thickness of strip. The thickness of strip may be as little as ten thousandths of an inch and as much as twenty thousandths of an inch. The laminates are contemplated to be in increments of two thousandths each.

10 Claims, 6 Drawing Figures

LAMINATED STRIP FOR SKIN THICKNESS CONTROL FOR USE WITH DERMATOME APPARATUS AND METHOD OF USING THE SAME

BACKGROUND OF THE INVENTION

1. Field of the Invention

With reference to the classification of art as established in and by the U.S. Patent Office the present invention is believed to be found in the general class entitled, "Surgery" (Class 128) and in the subclass entitled, "dermatome" (subclass 305.5).

2. Description of the Prior Art

Dermatome apparatus are well known and for many years the use of such apparatus has been a known means for removing a thin layer of skin. Most often this removed outer layer of skin is used to repair an area that needs new skin such as for a burn patient. The present invention utilizes the inexpensive dermatome shown in U.S. Pat. No. 4,098,278 as issued on July 4, 1978 to the present applicant. This patent and the dermatome shown and described therein employs a cutting blade which is moved by a holder which is of plastic or any moldable material that is inexpensive. The removed skin is preferably in a strip of determined width and length. A dermatome, through and in cooperation with an adhesive strip, is used to remove this skin. The adhesive strip used with the dermatome has an adhesive surface and a sliding surface.

Dermatomes, whether the one in applicant's reference patent or an expensive, large hospital device, must provide ready thickness control of the removed skin. The removed skin may vary from ten to twenty thousandths of an inch in thickess. These prior art devices have elaborate and expensive thickness control apparatus whereas the adhesive and laminated strip of the present invention provides ready means for the operator to select the thickness of the skin removed.

Several patents directed toward a mechanical assist for the removal of skin have issued. Among these patents some have been commercially produced and are used in hospitals. A powered knife with an adjustable thickness guide is shown in U.S. Pat. No. 1,594,613 to Hagen as issued on Aug. 3, 1926. A hand-powered knife with curved support and collecting unit is shown in U.S. Pat. No. 2,288,709 to Hood as issued on July 7, 1942. A similar and improved device is seen in U.S. Pat. No. 2,400,336 to Bishop as issued on May 14, 1946.

An elaborate device requiring vacuum is shown in U.S. Pat. No. 2,590,299. This retains the separated skin on a drum. In association with this drum, a powered knife blade is employed. This equipment is rather awkward to use, requires extensive preparation for sterilization and is expensive to procure and maintain. A vacuum source and usually pressurized air is required.

SUMMARY OF THE INVENTION

This invention may be summarized, at least in part, with reference to its object. It is an object of this invention to provide, and it does provide, an adhereing strip for use with a hand manipulated dermatome, said strip having a laminated portion enabling the operator to select the desired thickness of skin removed by the hand operated apparatus. The strip is used with the dermatome above referenced and is also color coded so that a predetermined thickness of skin is removed.

In brief this invention is directed toward and to adhesive strips as used with the dermatome apparatus of the referenced U.S. Pat. No. 4,098,278. The basic strip is provided with the adhesive surface and a removable covering as described in the reference patent. The main plastic member with the guide tongue is of a determined thickness, such as ten thousandths of an inch. Additional thicknesses in the strip are laminated and disposed with an adhesive coating and are placed on the upper surface of the pull strip. These thicknesses are each color coded so that with a known or given color exposed a known thickness of removed skin will be achieved with the use of the dermatome. The thickness of the laminates to be applied may be as many as five in number and as reduced-to-practice are each two thousandths of an inch in thickness. Each laminate thickness has a smooth outer sliding surface and when exposed presents a sliding surface to the curved surface on the dermatome. The adhesive surface on each laminate strip is disposed to be removed with its adhesive surface leaving an exposed sliding surface.

The dermatome apparatus disclosed in the reference patent and incorporated to the extent applicable in this application includes a hand held and operated device in which a blade is fixed as to a space between the cutting blade edge and a curved guide surface. The thickness of the plastic strip and the residual space of the cutting edge of the blade and the guide governs the resulting thickness of skin removed. The width of the plastic adhered strip, as and when the cut skin is severed by the reciprocating blade, establishes and governs the width of the skin strip removed.

In brief, this invention provides a dermatome apparatus which is furnished in a standard sterile condition in an inexpensive paper cover. One or more plastic strips are provided in this package. Each strip has a guide and a grasp end and adjacent this end is an extent of given width and length.

The cutting blade is of metal and is very similar to a razor blade in configuration except that it may be as long as five inches when the strip of skin to be removed is three inches wide. The blade is carried in a throwaway, plastic member which is formed with a guideway into which the blade extends a determined distance. This member has a grasping portion by which the member and the secured blade are moved back and forth in and with a reciprocating motion to cut the skin which is adhered to the plastic strip. The space in the guideway, the thickess of the plastic strip and adhesive and the projection of the blade into this space determines the resulting thickness of removed skin.

The plastic strip has been improved by the addition of a laminated portion carried with and on the base strip on which the grip and guide end is attached. The laminated area preferably has color coded thicknesses so that the user is visually able to compare with a chart to establish a desired thickness of skin removal. In addition to the above summary the following disclosure is detailed to insure adequacy and aid in understanding of the invention. This disclosure, however, is not intended to cover each new concept no matter how it may later be disguised by variations in form or additions of further improvements. For this reason there has been chosen a specific embodiment of the dermatome apparatus in its simplest arrangement as adopted for use for removing an outer portion of skin. With the dermatome apparatus an improved adhesive strip is shown with a laminated overlay and alternate means for easy removal of a particular laminate layer to produce a selected thickness of skin. The specific showings have been chosen for the purpose of description as shown in the accompanying drawings wherein:

BRIEF DESCRIPTION OF THE DRAWINGS

In the following description and in the claims details are identified by specific names for convenience. These names, however, are intended to be generic in their application. Corresponding reference characters refer to like members throughout the six figures of the drawings.

DESCRIPTION OF THE EMBODIMENT OF FIG. 1

Figure 1:
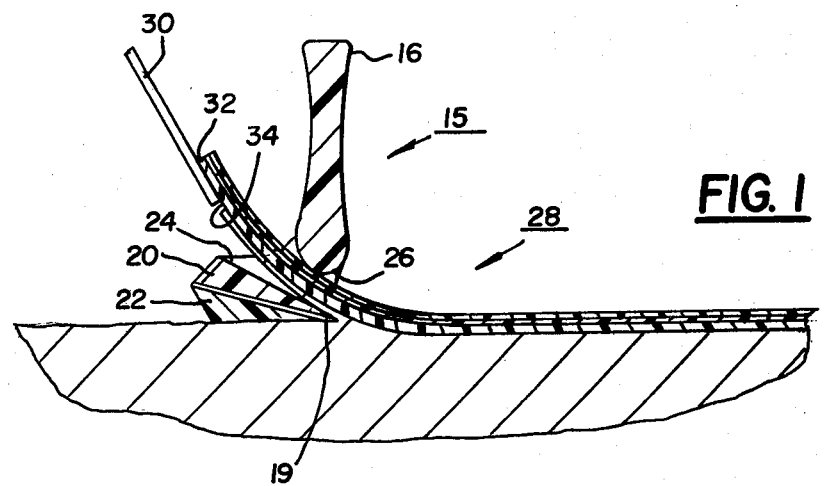
FIG. 1 represents a sectional view of the dermatome apparatus and showing a blade carrier and a plastic strip and the leading grasping tongue of the plastic strip, the strip shown with two laminate portions thereon and with the blade having separated a portion of skin from the body.

Referring next to the drawings and in particular to FIG. 1, there is depicted the simplest arrangement of a disposable dermatome. This apparatus is shown and more fully described in my above identified patent. To the extent applicable the numbers used in this patent have been carried forwardly but the numerals used with the laminated portion of the adhesive strip are not found in the reference patent.

As particularly seen in FIG. 1, this dermatome apparatus includes a blade holder generally identified as 15. A manipulating handle portion 16 is generally adapted for grasping by the user of the dermatome. A blade 19 is preferably of sharpened steel similar to that of an injector razor blade. This blade is retained in and by upper and lower guide members 20 and 22, usually of plastic. One guide member is usually integral with the handle portion and the other member is secured by a force fit into an appropriately formed guide. The other guide member may also be retained by cement. However secured, the blade 19 is positively retained in this dermatome apparatus.

The handle portion 16 and the blade 19, in combination with the upper and lower guides 20 and 22, provide a guideway 24 of a selected space or distance. A curve end 26 on the inner end of handle 16 provides a smooth surface for sliding on and over a plastic lift and guide strip member generally identified as 28. This strip member has a grasping tongue portion 30 which is tapered for entrance to and through guideway 24. This tongue is attached to or is a part of a midportion 32 which has the lower surface of this midportion coated with an adhesive surface 34. A release sheet or sheet portion 36 is placed on this adhesive portion until time for use. The width and length of the plastic strip midportion 32 and the adhesive portion thereof is the width and usually the length of skin to be removed. The thickness of midportion 32 in the guideway 24 between the cutting edge of blade 19 and the curved end 26 establishes the thickness of skin to be removed.

The thickness of the skin is easily governed by the use of the laminated adhesive strip. The removal of a determined number of layers leaves a total thickness of strip that is drawn through the guideway 24. This strip member with its laminated portion is more fully described in my U.S. Pat. No. 4,098,278, above identified.

PLASTIC LIFT AND GRASPING STRIP

Figure 2:
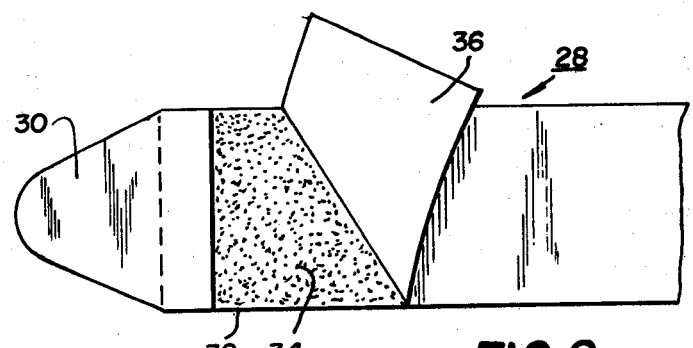
FIG. 2 represents a plan view, partly fragmentary, of a plastic stirp and showing the tongue, the adhesively coated midportion and a release sheet partly removed from the adhesively coated surface.
Figure 4:
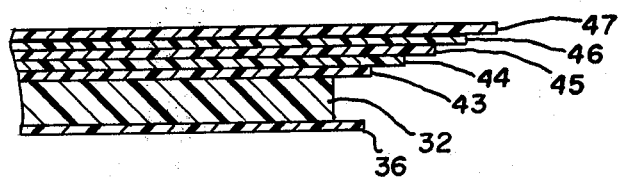
FIG. 4 represents an enlarged, sectional side view, taken on the line 4—4 of FIG. 3 and looking in the direction of the arrows.
Figure 3:
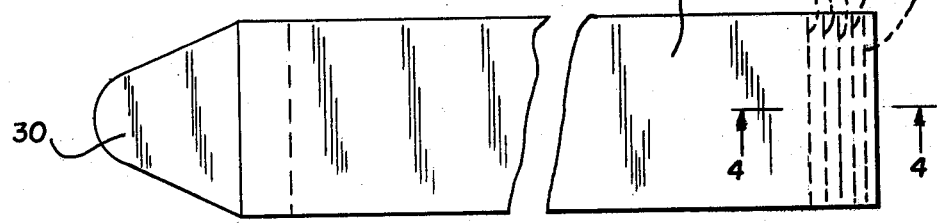
FIG. 3 represents a top view, partly diagrammatic, of the laminated plastic strip shown in FIG. 2.

Referring next to FIGS. 2, 3 and 4, there is depicted a plastic strip member that is used with the dermatome apparatus of FIG. 1. This strip member, in addition to the grasping tongue portion 30, includes the midportion 32 which is preferably ten thousandths of an inch in thickness. The lower surface has the adhesive surface 34 and the release sheet or portion 36 as in the reference patent. The surface above this strip member includes a laminated structure with plastic strips of determined thickness. Above midportion 32 there is shown a laminate generally identified as 42. Laminate portions 43, 44, 45, 46 and 47 are shown and are preferably two thousandths of an inch in thickness. Each laminate strip member is preferably of a different color and with a chart furnished with the dermatome enables the user to immediately expose a given color to provide a given thickness of skin.

Each laminate has one surface provided with a thin but effective adhesive coating to retain the film laminate strip to the immediately below strip. This adhesive coating is identified as 43a, 44a, 45a, 46a, and 47a and is only sufficient to retain the plastic strip members to the immediately below member. When a given laminate layer is removed the exposed top surface is smooth and provides a sliding surface for the curve end 26 to slide over and along said surface.

USE AND OPERATION

In use the surgeon or attendant who is to perform the skin removal prepares the skin surface selected in the usual manner. The midportion 32 of the plastic strip is cut or otherwise is selected as to the width and length. The thickness of the plastic strip is also selected by the surgeon or attendant by using the midportion 32 and the laminated portion so as to provide a desired thickness of removed skin. The released sheet portion or portions 36, as shown in FIG. 1, are removed from the adhesive surface 34 and this exposed adhesive portion is placed on a body portion (FIG. 1). The tongue portion 30 is guided through guideway 24 and with one hand grasping this tongue portion the holder 15 is moved by the other hand to produce a cutting action by the blade 19. As seen in FIG. 1, this results in a thin portion of skin 40 which is cut from the body member 38 by the guided action of blade 19.

After cutting the desired area of skin, the plastic strip with this removed skin is then severed from the patient and is transferred to the area to be treated. The removed skin and plastic may be cut into desired strips or the skin may be removed from the adhesive portion of the plastic strip and then tailored for application to the body area to be treated.

REMOVAL OF LAMINATE STRIP PORTIONS

In FIG. 2 the exposed portion of the strip shows the adhesive surface 34 and the release sheet 36. This release sheet may also be extended a short distance to the rear extent of midportion 32. This extension of the release sheet 36 enables the user of the dermatome to remove the release sheet 36 from either end of midportion 32. As seen in FIG. 4, the laminates 43, 44, 45, 46 and 47 are each made progressively longer so that the desired laminate layer can and is left attached to the midportion 32. Preferably each laminate has a different color so that the desired thickness of laminate remains to provide a given thickness of skin removal.

LAMINATED GUIDE AND LIFT STRIP OF FIGS. 5 AND 6

Figure 5:
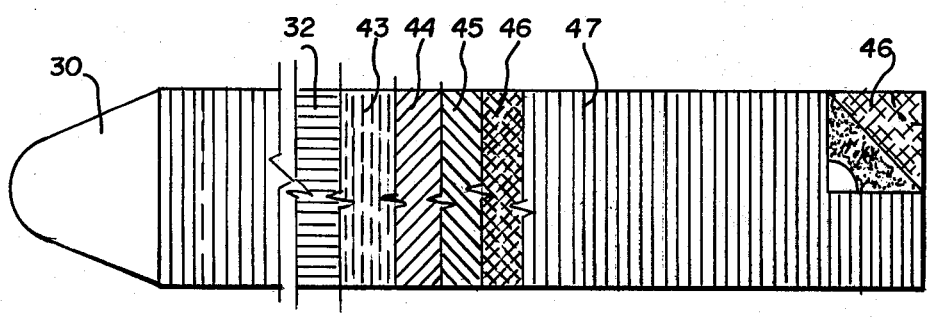
FIG. 5 represents a plan view, partly diagrammatic, and showing the plastic strip with the laminate portion shown as layers in color coded array and with the several layers having a corner with no adhesive to provide an easy access means for removing the laminate strips from the midportion strip and, FIG. 6 represents a side view in a greatly enlarged scale and showing a color coding of the laminates making up the laminated portion of the strip, and showing also the midportion and release sheet of said plastic lift and guide strip.
Figure 6:
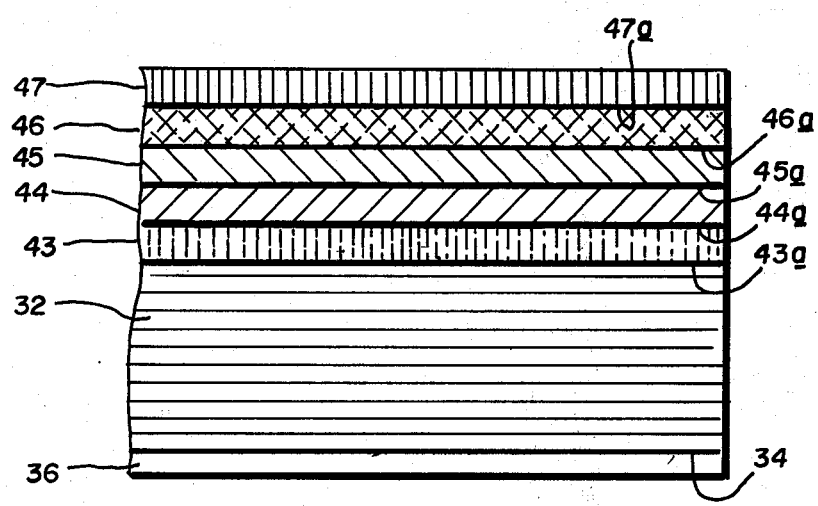

Referring next and finally to FIGS. 5 and 6, there is illustrated a guide and lift strip generally identified as 28. In this embodiment the midportion 32 is preferably of plastic of about ten thousandths of an inch in thickness. This plastic is colored and, as illustrated, is shown as blue in color. A lower surface has adhesive 34 except for a corner (upper right) which has no adhesive to assist in the easy grasping for lifting and removal of the release sheet portion 36. Laminate portions 43, 44, 45, 46 and 47 are much thinner, such as two thousandths of an inch, and are color coded. As depicted, laminate layer 43 is shown as purple. Laminate layer 44 immediately above is shown with a brown color. Laminate layer 45 immediately above layer 44 is shown as green. Laminate layer 46 which is immediately above 45 is shown as orange. The top laminate layer 47 is shown as pink.

The color coding shown is only a representation since the several layers may be colored to suit preferences by the manufacturer. The several laminates each have their bottom engaging surfaces coated with an adhesive sufficient to cause the above laminate to be retained in place while the dermatome apparatus above described is used.

This dermatome apparatus is adapted for one person operation and the use of inexpensive components anticipate the discarding after use. The size of the adhesively coated plastic strip determines the maximum area of skin to be removed with one plastic strip. More than one strip may be used, of course. If more than one strip is to be used, the strips may be applied as the blade holder is moved from one attached strip to the next. The removed skin may be kept with the strip until all the skin to be removed is on the several strips of adhesively coated plastic.

The concept of a blade holder, above described, is disposed to be used with strips of plastic of determined thickness such as ten to twenty thousandths of an inch. The midportion plastic strip has a given width and length to which a special skin adhering adhesive is applied and also a released sheet. Each strip has a grasping tongue which is tapered for ease of entry into a guideway in the blade holder. The strip of plastic may be cut to a smaller width and length, if desired. The thickness of skin cut from the body of the patient is directly related to the space in the guideway, the thickness of plastic strip and the positioning of the cutting edge of the blade from the curved surface forming one side of the guideway. The thickness of the plastic film strip and the cut skin is equal to this guideway space. The laminates provide means for readily establishing a thickness of skin to be removed with an appropriate and complementary thickness of laminated guide and lift strip. The dermatome apparatus may be used to remove several strips of skin but it is contemplated that a separate guide and lift strip will be used with each skin strip to be removed. The thickness of skin may also be changed for each to be removed strip of skin since areas to be treated may required different thicknesses.

The laminated portion of the strip 28, as above described, is color coded with thicknesses and colors indicated. The laminates may be of varying thicknesses and, of course, may be of any color including nearly transparent. It is also contemplated that only a small portion of the laminated layers may be color coded or as an alternate, may have numerals or letters readily identifiable to provide the desired information as to thickness of the film strip and or skin thickness that is to be removed by the dermatome. Particular applications and uses may require thicknesses greater or lesser than those discussed. The layered laminate enables the user to readily provide the desired thickness of skin to be removed. The width of the adhered strip establishes the width of removed skin so that a narrower strip is easily provided by cutting the adhesive strip lengthwise. Length or extent of skin removal is readily determined by observation. The laminates and midportions, of course, can be of the same or different thicknesses and also the removal of adhesive as described and shown in FIG. 6 may be in areas other than in a corner. Removal of said adhesive in other areas for manipulative removal of a desired laminate thickness is merely a matter of preference.

The above dermatome apparatus lends itself to a novel method in which the steps of removing a thin piece of skin of a given size from a body member utilizes this apparatus for achieving the needed steps. As a method, the above apparatus, for a one-time use by the attendant or surgeon, includes the steps of providing a blade holder having a handle portion for grasping and moving the holder in and with a back and forth reciprocating motion; mounting and carrying a blade having a sharpened edge in and by said holder and with the blade movable with the holder as it is moved; forming a guideway in the blade holder and extending into this guideway the sharpened blade to define a determined spaced slot; forming a curved portion on an inner edge of the blade holder and defining a side of the guideway into which the blade enters; in combination with this blade holder there is also a forming and providing of a plastic strip including a tongue which is tapered to provide an easy entering portion into and through the guideway in the blade holder; this strip having a midportion of determined width, length and thickness; applying an adhesive surface to this midportion of the plastic strip and on one side thereof and providing thereby an adhesive attraction to that portion of skin to be removed, and placing a release sheet on the adhesive surface and providing therewith a protection for said adhesive surface until the release sheet is removed for placing the adhesive face of the strip on the skin to be removed, placing on the upper surface of this midportion a laminated assembly of plastic strips, color coded as to each strip and providing an adhesive means for maintaining each strip in assembled array as and until a desired array of laminated strips are removed by the attendant; the cutting of and removal of the outer skin being accomplished by a back and forth reciprocating movement of the blade holder after threading the tongue of the plastic strip and remaining laminates through the guideway of the blade holder and positioning the holder with the blade edge toward the adhered plastic strip and with a cutting by a reciprocating motion of the blade the plastic strip and thickness of adhered plastic laminated strip is equal to the spaced slot in the guideway.

Terms such as "left," "right," "up," "down," "top," "front," "back," "in," "out" and the like are applicable to the embodiment shown and described in conjunction with the drawings. These terms are merely for the purposes of description and do not necessarily apply to the position in which the dermatome apparatus and its portable plastic strips may be constructed or used.

While a particular embodiment of the dermatome apparatus and improved laminated strip and method have been shown and described it is to be understood the invention is not limited thereto since modifications may be made within the scope of the accompanying claims and protection is sought to be broadest extent the prior art allows.

What is claimed is:

1. A dermatome apparatus combination adapted for a onetime use and operation by one person such as a surgeon or attendant for the removal of a selected area of skin of a determined thickness from a patient, this apparatus combination with a blade holder having a handle portion for assisting with grasping and moving the holder in and with a reciprocating motion; a blade having a sharpened edge and carried in and by said holder and movable with the holder as it is moved, said reciprocating motion being parallel to said sharpened blade edge; a guideway of a selected opening formed in the blade holder and with the sharpened edge of the blade projecting forwardly adjacent the bottom of the guideway to define a determined spaced opening; a curved portion provided by the blade holder and defining a side of the guideway into which said cutting edge of the blade enters, the cutting edge of the blade being substantially parallel to the curved portion; and in association and combination with said blade holder an improved plastic strip including: (a) a tongue end which is tapered to provide an easy entering portion into and through the guideway in the blade holder, the strip having a midportion of plastic and of determined width, length and thickness, this width of the midportion being substantially less than the length of the guideway in the blade holder so that reciprocation of the blade holder can occur while the plastic strip is in the guideway; (b) an adhesive surface applied to this midportion of the plastic strip and on one side thereof to provide an adhesive attraction to that portion of skin to be removed by a cutting action of the blade; (c) a release sheet applied to the surface and providing a protection for said adhesive surface until removed for placing the adhesive face of the strip on the skin to be removed from the patent; (d) a laminated assembly of plastic strips adhesively releasably carried with and by said midportion plastic strip, said midportion strip and the layered laminated strips so structured and adhered that the plastic strip exposed and opposite the adhesive surface for retaining the skin is smooth and provides a sliding surface over and on which the curved portion of the holder slides, and (e) means for engaging and manipulating the removal of a selected laminate to provide a determined thickness of plastic strip so that the cutting of and removal of the outer skin may be accomplished by a reciprocating movement of the blade holder and blade after threading the tongue of the plastic strip through the guideway of the blade holder and after pressing the adhesively coated portion of the strip to the skin of the patient with the holder positioned with the blade edge toward the adhered plastic strip on the skin and with the adhered skin lifted whereby a cutting motion of the blade allows the plastic strip and thickness of adhered, removed skin to be pulled through the guideway, the combination of the laminated plastic strip and removed skin being of a thickness equal to the spaced opening in the guideway.

2. An improved laminated plastic strip for use with a hand held and operated dermatome as in claim 1 in which the midportion strip is about ten thousandths of an inch in thickness and the laminate layers are about two thousandths of an inch in thickness.

3. An improved laminated plastic strip for use with a hand held and operated dermatome as in claim 1 in which the midportion strip has a selected color and the several layers comprising the laminate are each colored with different colors to enable a color chart to be consulted and a determined thickness of strip to be readily ascertained.

4. An improved laminated plastic strip for use with a hand held and operated dermatome as in claim 1 in which the midportion strip and layered laminated strips have different lengths to enable the user to readily remove the unwanted laminate strip portions.

5. An improved laminated plastic strip for use with a hand held and operated dermatome as in claim 1 in which the midportion strip and layered laminated strips have a small portion with no adhesive to allow separation and ready removal of unwanted laminate strip portions.

6. A method for removing a thin layer of skin with the assist of an apparatus combination adapted for a one-time use and operation by one person such as a surgeon or attendant, the removal of a selected area of skin of a determined thickness from a patient through the use of a blade holder having a handle portion which is used to move the holder and a sharpened blade carried thereby, the holder having a guideway of a selected width and length and with the sharpened edge of the blade projecting forwardly adjacent the bottom of the guideway to define a determined spaced opening, the blade holder further having a curved portion on an inner edge, this curved portion being substantially parallel to the cutting edge and in association and combination with said blade holder forming and providing a laminated plastic strip including a tongue which is tapered to provide an easy entering portion into and through the guideway in the blade holder, this strip having a midportion of determined width, length and thickness, this width of the midportion being substantially less than the length of the guideway opening in the blade holder, this strip having an adhesive surface on said midportion of the plastic strip and on one side thereof and providing therewith an adhesive attraction to that portion of skin to which it is pressed, the laminated plastic strip having its midportion and all above and releasably secured layered laminate portions adapted so that the surface opposite the adhesive surface as and when exposed provides a slidable surface, said plastic strip having a release sheet on the adhesive surface and providing therewith a protection for said adhesive surface until the release sheet is removed for placing the adhesive face of the strip on the skin to be removed from the patient, the cutting of and removal of the outer skin being accomplished by the steps of: (a) removing the release sheet from the adhesively coated side of the midportion strip of plastic; (b) pressing the adhesively coated portion of the strip of plastic to that skin portion of the patient that is to be removed; (c) threading the tongue portion of the laminated plastic strip with and of a selected thickness through the guideway of the blade holder so that the outer and upper exposed surface of said laminated strip is in sliding and guiding contact with the curved portion of the blade holder, and (d) cutting of and removal of the outer skin by reciprocating the blade holder in a motion parallel to the cutting edge of the blade so that the plastic strip and thickness of adhered, removed skin as a composite strip is pulled through the guideway, the combination of the plastic strip and removed skin being of a thickness equal to the spaced opening in the guideway.

7. A method of skin removal as in claim 6 which includes the further step of preparing the laminated strip to provide the selected thickness by removing a selected number of layers of laminates so as to provide the desired thickness of plastic strip.

8. A method of skin removal as in claim 7 which includes the step of selecting the selected thickness by removing laminates in accordance with a color coding chart.

9. A method of skin removal as in claim 6 which includes forming the laminated plastic strip with portions having no adhesive so that ease of removal of laminated portions is easily accomplished.

10. A dermatome apparatus which utilizes an improved plastic strip and adapted for the removal of a selected area of skin of a determined thickness from a patient, this dermatome having a blade holder and means for moving the holder in and with a reciprocating motion, said blade having a sharpened edge and carried in and by said holder and movable with the holder as it is moved, said reciprocating motion being parallel to said sharpened blade and with said dermatome having a guideway providing a selected opening in the blade holder and with the sharpened edge of the blade projecting toward the guideway and establishing with the holder a determined spaced opening, said holder providing a guideway portion and defining a side of the guideway into which said cutting edge of the blade enters, the cutting edge of the blade being substantially parallel to the guideway, and in association with the dermatome, an improved plastic strip includes: (a) a tongue end which is tapered to provide an easy entering portion into and through said guideway in the blade holder, the strip having a midportion of plastic and of determined width, length and thickness, this width of the midportion being substantially less than the length of the guideway in the blade holder as that reciprocation of the blade holder can occur while the plastic strip is in the guideway; (b) an adhesive surface applied to this midportion of the plastic strip and on one side thereof to provide an adhesive attraction to that portion of skin to be removed by a cutting action of the blade; (c) a release sheet applied to the surface and providing a protection for said adhesive surface until removed for placing the adhesive face of the strip on the skin to be removed from the patient; (d) a laminated assembly of plastic strip, said midportion strip and the layered laminated strips so structured and adhered that the plastic strip exposed and opposite the adhesive surface for retaining the skin is smooth and provides a sliding surface over and on which the curved portion of the holder slides, and (e) means for engaging and manipulating the removal of a selected laminate to provide a determined thickness of plastic strip so that the cutting of and removal of the outer skin may be accomplished by a reciprocating movement of the blade holder and blade after threading the tongue of the plastic strip through the guideway of the blade holder and after pressing the adhesively coated portion of the strip to the skin of the patient with the holder positioned with the blade edge toward the adhered plastic strip on the skin and with the adhered skin lifted whereby a cutting motion of the blade allows the plastic strip and thickness of adhered, removed skin to be pulled through the guideway, the combination of the laminated plastic strip and removed skin being of a thickness equal to the spaced opening in the guideway.

* * * * *